United States Patent [19]

Bröecker et al.

[11] Patent Number: 4,600,799

[45] Date of Patent: Jul. 15, 1986

[54] PREPARATION OF TRIMETHYLHYDROQUINONE

[75] Inventors: Franz J. Bröecker, Ludwigshafen; Peter Tavs, Limburgerhof; Harald Laas, Maxdorf; Wolf-Karlo Aders, Ellerstadt, all of Fed. Rep. of Germany

[73] Assignee: BASF Aktiengesellschaft, Ludwigshafen, Fed. Rep. of Germany

[21] Appl. No.: 699,194

[22] Filed: Feb. 7, 1985

[30] Foreign Application Priority Data

Feb. 8, 1984 [DE] Fed. Rep. of Germany ....... 3404337

[51] Int. Cl.$^4$ .............................................. C07C 37/07
[52] U.S. Cl. ..................................... 568/772; 568/799
[58] Field of Search ................................. 568/772, 799

[56] References Cited

U.S. PATENT DOCUMENTS

| 2,229,573 | 1/1941 | Jung | 568/772 |
| 2,229,574 | 1/1941 | Jung | 568/772 |
| 3,723,541 | 3/1973 | Schuster et al. | 568/772 |
| 3,839,468 | 1/1974 | Tamai et al. | 568/772 |
| 3,842,130 | 10/1974 | Kawaguchi et al. | 568/772 |
| 3,954,891 | 5/1976 | Orth et al. | 568/772 |

FOREIGN PATENT DOCUMENTS

| 1940386 | 4/1971 | Fed. Rep. of Germany | 568/772 |
| 1956381 | 5/1971 | Fed. Rep. of Germany | . |
| 2309051 | 2/1973 | Fed. Rep. of Germany | 568/772 |
| 2250066 | 5/1973 | Fed. Rep. of Germany | 568/772 |
| 7011586 | 2/1971 | Netherlands | 568/772 |

*Primary Examiner*—Werren B. Lone
*Attorney, Agent, or Firm*—Keil & Weinkauf

[57] ABSTRACT

2,3,6-Trimethylhydroquinone is prepared by catalytic hydrogenation of 2,3,6-trimethylquinone with hydrogen in the presence of a solvent by a continuous process in which the reaction is carried out over a platinum-/alumina catalyst.

8 Claims, No Drawings

PREPARATION OF TRIMETHYLHYDROQUINONE

The present invention relates to a process for the continuous preparation of highly pure 2,3,6-trimethylhydroquinone by catalytic hydrogenation with hydrogen, in the presence of a solvent, over a platinum-/alumina catalyst.

2,3,6-trimethylhydroquinone is an intermediate for the preparation of vitamin E. Methods for the preparation of 2,3,6-trimethylhydroquinone are known. For example, quinones can usually be reduced to hydroquinones with iron powder in a solution containing sulfuric acid, or with sodium bisulfate. These procedures give undesirable sulfate solutions as by-products, which make the process uneconomical. A process for the preparation of trimethylhydroquinone by catalytic reduction of trimethylquinone with hydrogen and in the presence of a hydrogenation catalyst, wherein the reaction is carried out using an aliphatic alcohol of 3 to 5 carbon atoms as a solvent, is also known.

In a continuous procedure, as described in German Laid-Open Application DOS No. 1,940,386, the concentration of the by-products increases continuously when the alcohol used as a solvent is recycled, so that some of the mother liquor has to be separated off. This results in losses of useful product.

Even the process described in German Laid-Open Application DOS No. 2,250,066, for the preparation of 2,3,5-trimethylhydroquinone by catalytic hydrogenation of 2,3,5-trimethylbenzoquinone with hydrogen in an organic carboxylate as a solvent, gives an appropriately pure product only after a precipitation which is very expensive to carry out industrially on a large scale.

Furthermore, a process for the preparation of hydroquinones by reduction of the quinones with hydrogen in the presence of a copper chromite catalyst under from 10 to 300 bar and at from 20° to 300° C. is described in German Laid-Open Application DOS No. 1,956,381. In this process, too, the hydroquinones obtained are not sufficiently pure, so that the hydrogenation product still has to be recrystallized after the solvent has been evaporated off, in order to obtain the required purity. Furthermore, in order to avoid discoloration, a stabilizer has to be added to the hydroquinone obtained in this manner.

It is an object of the present invention to provide a simple hydrogenation process in which the formation of by-products during the hydrogenation is suppressed, and the purification measures for the hydrogenation product which have been described therefore become superfluous.

We have found that this object is achieved, and that 2,3,6-trimethylhydroquinone can be prepared by a continuous procedure by catalytic hydrogenation of 2,3,6-trimethylquinone with hydrogen in the presence of a solvent, if the reaction is carried out over a platinum-/alumina catalyst.

Because of the excellent selectivity of this catalyst, the solvent can be separated off from the hydrogenated mixture by simple evaporation, and the resulting 2,3,6-trimethylhydroquinone need not be subjected to any further purification. The basis of the novel process is a catalyst which possesses 100% selectivity and therefore does not produce any by-products at all. This makes possible a continuous process in which, simply by evaporating off the solvent, highly pure crystalline 2,3,6-trimethylhydroquinone is obtained which does not become discolored on prolonged storage. By dispensing with the expensive purification processes, the industrial hydroquinone preparation is substantially improved. In contrast to the conventional process in which, as a result of the by-products being separated off, useful products too are always lost, there is no loss of useful product in the process according to the invention. Deactivation of the catalyst is avoided, so that the novel process also results in a long catalyst life.

In the preparation of the novel $Pt/Al_2O_3$ catalyst, a particular BET specific surface area and a defined pore distribution are important. The catalyst according to the invention is based on a carrier of alumina, preferably $\gamma$-$Al_2O_3$, having a BET surface area of from 1 to 350, preferably from 10 to 300, in particular from 200 to 270 $m^2/g$ and a pore volume of from 0.35 to 0.60, in particular from 0.45 to 0.55, $cm^3/g$ in the pore radius range from 1.8 to 60,000 nm, with the proviso that not less than 60%, preferably from 80 to 90%, of the pore volume is in the pore radius range from 2 to 200, preferably from 2 to 100, nm.

To prepare this special carrier, aluminum hydroxide, $Al(OH)_3$, is precipitated, dried and converted to moldings by pressing or extruding, and the moldings are then calcined at from 300° to 1,200° C., preferably from 400° to 1,150° C., in particular from 400° to 600° C. This calcination is carried out so that the resulting carrier is characterized by the physical data stated above. The carrier obtained in this manner is then impregnated with an aqueous platinum nitrate solution so that a catalyst containing from 0.01 to 0.5, preferably from 0.05 to 0.15, % by weight of Pt is obtained. The amount of solution for impregnating the carrier corresponds to 90% of the water absorption capacity of the carrier. The carrier is impregnated with this amount of solution, for example in a coating drum, and dried at from 100° to 150° C., preferably from 110° to 130° C., and then calcined at from 180° to 250° C. The resulting catalyst is introduced into a fixed-bed hydrogenation reactor and reduced with hydrogen for from 0.5 to 6 h at from 50° to 200° C., preferably 100° C. Thereafter, a solution of 2,3,6-trimethylquinone in isobutyl alcohol is passed over the catalyst at from 80° to 110° C., preferably from 95° to 105° C., and under a hydrogen partial pressure of 1 bar. The hydrogenation product is freed from solvent in a rotary evaporator and then analyzed. The space velocity in this hydrogenation is from 0.05 to 0.6, in particular from 0.1 to 0.25, kg of trimethylquinone per L of catalyst per hour.

The hydrogenation can be carried out by a liquid-phase or trickle-bed procedure, alcohols being particularly suitable solvents. In the trickle-bed procedure, it is advantageous to use a superficial velocity of only 20–80 $m^3.m^2.h^{-1}$. The reflux ratio ($R_v$=weight of reflux/weight of feed) is from 10 to 65, and the space velocity is about 0.05–0.6 kg of trimethylquinone per l of catalyst per hour, based on trimethylquinone. By means of a heat exchanger in the hydrogenation cycle, the temperature at the reactor entrance can be adjusted to 80°–120° C. The hydrogen partial pressure in the hydrogenation of trimethylquinone is about 0.5–5 bar. To prevent the concentration of inert substances from increasing, a certain amount of exit gas can be removed. The amount of exit gas is advantageously such that the content of inert substances does not exceed from 5 to 10 vol. %.

EXAMPLE 1

Hydrargillite, Al(OH)$_3$, is precipitated from an aluminum nitrate solution with dilute sodium hydroxide solution, and the precipitate is washed, and dried at from 100° to 150° C. The dry product is milled in a ball mill and then converted to a paste with water in a kneader. This paste is converted to 3 mm extrudates using an extruder, and the extrudates are dried at 120° C. and then calcined for 5 hours at 450° C. in a muffle furnace. The resulting γ-Al$_2$O$_3$ has a BET surface area of 254 m$^2$/g and a pore volume of 0.521 cm$^3$/g in the pore radius range from 1.8 to 60,000 nm, 85% of the pore volume being in the pore radius range from 2 to 100 nm.

An aqueous solution of 1.79 g of platinum(II) nitrate (55.87% by weight of Pt) from Heraeus, in 610 ml of water, is added to 1 kg of this carrier, in the form of 3 mm extrudates, in a coating drum. The amount of solution corresponds to about 90% of the water absorption capacity of the carrier. The carrier and the solution are agitated in the coating drum for from 15 to 20 minutes, so that the liquid is uniformly absorbed by the carrier. The moist catalyst is then dried at 120° C. for 16 hours, after which it is calcined for 8 hours at 200° C. The catalyst contains 0.1% by weight of platinum.

100 ml of this catalyst are introduced into a hydrogenation reactor and heated at 100° C. under nitrogen. When this temperature is reached, the nitrogen is replaced with hydrogen, and the catalyst is reduced with H$_2$ for 1 hour. Thereafter, a 20% strength solution of 2,3,6-trimethylquinone in isobutanol is passed over the catalyst, and the amount of exit gas is adjusted to 1.2 l/h. The temperature is kept at 100° C. The space velocity is 0.135 kg of trimethylquinone per l of catalyst per hour, based on 2,3,6-trimethylquinone. The hydrogenation product is freed from solvent in a rotary evaporator and then analyzed. The conversion, based on 2,3,6-trimethylquinone, the yield and therefore also the selectively are each 100%. The resulting white 2,3,6-trimethylhydroquinone does not change in color on storage since it is very pure.

In order to compare the catalysts according to the invention with other catalysts, the following experiments were carried out:

EXPERIMENT 1

Effect of the carrier

A platinum catalyst containing active carbon as a carrier is prepared. To do this, a solution of 0.72 g of platinum(II) nitrate (55.87% by weight of Pt) in 480 ml of distilled water is added to 400 g of active carbon in the form of 4 mm extrudates, and the mixture is agitated for 10 minutes in a coating drum. The moist catalyst is then dried for 18 hours at 120° C. and heated for a further 6 hours at 200° C.

Using a procedure similar to that described in the Example, this catalyst is reduced with 0.1% by weight of Pt on active carbon, and is used for the hydrogenation of 2,3,6-trimethylquinone. After the solvent has been evaporated off, the hydroquinone is analyzed, the following result being obtained:

| | |
|---|---|
| Conversion: | 99.8% |
| Yield: | 92.6% |
| Selectivity: | 92.8% |

The Example shows that substantial amounts of by-products are formed.

EXPERIMENT 2

Palladium as the active component

A commercial palladium catalyst containing 0.5% by weight of Pd on SiO$_2$ as a carrier is employed, and hydrogenation is carried out similarly to the Example. Under the standard conditions stated, the following result is obtained:

| | |
|---|---|
| Conversion of trimethylquinone: | 98.6% |
| Yield of trimethylhydroquinone: | 91.8% |
| Selectivity: | 93.1%. |

EXPERIMENT 3

Palladium as the active component 3 mm alumina extrudates are prepared as described in Example 1 and then heated for 7 hours at 1,050° C. The resulting carrier has a BET surface areas of 25 m$^2$/g and a pore volume of 0.380 cm$^3$/g in the pore radius range from 1.8 to 60,000 nm, 80% of this volume being in the pore radius range from 2 to 100 nm.

800 g of this carrier are impregnated with a solution of 36.36 g of palladium nitrate solution (11% by weight) and 310 ml of distilled water, and agitated for 10 minutes in a coating drum. The moist catalyst is then dried for 7 hours at 120° C. and heated for 12 hours at 200° C. The resulting catalyst contains 0.5% by weight of Pd on alumina as a carrier. 100 ml of this catalyst are used for the hydrogenation under the conditions described in the Example. The following result is obtained:

| | |
|---|---|
| Conversion of trimethylquinone: | 99.8% |
| Yield of trimethylhydroquinone: | 92.7% |
| Selectivity: | 92.9%. |

Experiments 2 and 3 show that palladium gives substantial amounts of by-products, even when Al$_2$O$_3$ is used as the carrier. 100% selectivity is achievable only with platinum as the active amount and Al$_2$O$_3$ as the carrier. This result is surprising since, according to Germain Laid-Open Application DOS No. 1,956,381, supported noble metal catalysts have only a very short life.

EXAMPLE 2

Aluminum hydroxide paste is prepared as described in Example 1 and pressed to give moldings, which are dried, and then calcined for 5 hours at 1,100° C. The resulting α-Al$_2$O$_3$ has a BET surface area of 12 m$^2$/g and a pore volume of 0.520 cm$^3$/g in the pore radius range from 1.8 to 60,000 nm, 70% of the pore volume being in the radius range from 2 to 100 nm.

A solution of 2.17 g of platinum(II) nitrate (55.22% by weight of Pt) in 500 ml of distilled water is added to 1.2 kg of this carrier in a coating drum. The drum is agitated for 10 minutes, after which the moist catalyst is dried for 8 hours at 120° C. and then heated for a further 8 hours at 200° C. The catalyst obtained in this manner contains 0.1% by weight of Pt on α-Al$_2$O$_3$.

100 ml of this catalyst are reduced by a method similar to that described in Example 1, and then used for the hydrogenation of 2,3,6-trimethylquinone. Under the conditions stated in Example 1, and with a space velocity of 0.135 kg of trimethylquinone per l of catalyst per hour, the following results are obtained in the hydrogenation:

|  |  |
|---|---|
| Conversion: | 98.4% |
| Yield: | 98.4% |
| Selectivity: | 100%. |

Here too, the selectivity is 100%, whereas the smaller BET surface area results in the conversion being lower than that in Example 1.

EXAMPLE 3

Experiments relating to the catalyst activity over a prolonged period are carried out using a test apparatus for continuous hydrogenation. The apparatus consists of a vertical tube (about 3.0×130 cm) as the hydrogenation reactor, which is heated externally. A separator having a capacity of about 3 l is located below the tube.

Hydrogenation solution is circulated from the separator, and fresh solvent, 2,3,6-trimethylquinone and hydrogen are metered in at the upper end of the tube. The solution runs over the catalyst bed and collects in the separator. Exit gas and liquid are removed continuously from the separator.

755 g of catalyst, as described in Example 1, are introduced into the hydrogenation reactor and reduced in a stream of hydrogen with simultaneous circulation of 50 l/h of isobutanol. All of the experiments described below are carried out using a hydrogen pressure of about 2 bar at the upper end of the hydrogenation reactor and 50±10 l/h of recycle liquid. 145 g/h of trimethylquinone and 720 ml/h of isobutanol are first metered in, and the trimethylquinone feed is then increased in several stages to 690 g/h, and the amount of isobutanol is increased to 3,400 ml/h.

This corresponds to a space velocity of from 0.192 to 0.914 g of trimethylquinone per g of catalyst per hour.

No trimethylquinone (<0.1% by weight) can be detected in the reacted mixture by gas chromatography.

The hydrogenation is then operated with a constant feed (160 g/h of trimethylquinone and 790 ml/h of isobutanol), a total of 71.42 kg of trimethylquinone having a purity of about 99.25% by weight are fed in. The reacted mixture is evaporated down, and 72.12 kg of 99.6% pure 2,3,6-trimethylhydroquinone are obtained. The selectively of the conversion of trimethylquinone to trimethylhydroquinone is 100%. Even after 446 hours, the selectivity is still 14%. A decrease in the activity of the catalyst is not found.

We claim:

1. A continuous process for the preparation of 2,3,6-trimethylhydroquinone by catalytic hydrogenation of 2,3,6-trimethylquinone with hydrogen in the presence of a solvent, wherein the reaction is carried out over a platinum/alumina catalyst, and
    wherein the alumina carrier has a BET surface area of from 1 to 350 $m^2/g$ and a pore volume of from 0.35 to 0.60 $cm^3/g$ in the pore radius range from 1.8 to 60,000 nm, not less than 60% of this pore volume being constituted by pores having a radius of from 2 to 200 nm.

2. A process as claimed in claim 1, wherein the reaction is carried out under a hydrogen partial pressure of from 0.5 to 5 bar and at from 80° to 120° C.

3. A process as claimed in claim 1, wherein the solvent is evaporated off from the hydrogenation product and recycled to the process.

4. The process of claim 1, wherein the alumina carrier has a BET surface area from 10 to 300 $m^2/g$.

5. The process of claim 1, wherein the alumina carrier has a BET surface area of 200 to 270 $m^2/g$.

6. The process of claim 1, wherein the alumina carrier has a pore volume of from 0.45 to 0.55 $cm^3/g$.

7. The process of claim 1, wherein the pore volume has 80–90% in the pore radius range of from 1.8 to 60,000 nm.

8. The process of claim 7, wherein the pore radius range is from 2 to 100 nm.

* * * * *